United States Patent [19]
Preti et al.

[11] Patent Number: 5,538,719
[45] Date of Patent: Jul. 23, 1996

[54] METHOD FOR REDUCING PERCEPTION OF HUMAN UNDERARM ODOR BY A PLEASANT SMELLING COMPOUND

[75] Inventors: George Preti, Horsham; John D. Pierce, Jr., Havertown; Xiao-Nong Zeng, Jenkingtown, all of Pa.; Charles J. Wysocki, Collingswood, N.J.

[73] Assignee: Monell Chemical Senses Center, Philadelphia, Pa.

[21] Appl. No.: 218,309

[22] Filed: Mar. 25, 1994

Related U.S. Application Data

[63] Continuation-in-part of Ser. No. 67,672, May 26, 1993.

[51] Int. Cl.[6] .................................. A61K 7/32; A61K 7/46
[52] U.S. Cl. ..................................... 424/65; 512/25
[58] Field of Search ......................... 512/25; 424/65

[56] References Cited

PUBLICATIONS

Engen, *The Perception of Odors*, Academic Press, New York (1982); Moncrieff, "Olfactory adaptation and odour likeness," J. Physiol., 133:301–316 (1956).
Cain, "Odor intensity after self–adaptation and cross–adaptation," Percept. Psychophys., 7:271–275 (1970).
Engen & Lindstrom, "Cross–adaptation to the aliphatic alcohols," Amer. J. Psych., 76:96–102 (1963).
Pierce, Wysocki & Aronov, "Mutual cross–adaptation of the volatile steroid . . ." (in Oxford Unversity Press) vol. 13 No. 3 pp. 245–256 (1956).
Todrank, et al., "The effects of adaptation on the perception of similar and dissimilar odors," *Chem. Senses*, 16:467–482 (1991).
Engen, *The Perception of Odors*, Academic Press, New York (1982); Moncrieff, "Adaptation—Definition of the Problem," Chapter 4:61–77.
Koster, "Adaptation and cross–adaptation in olfaction," Doctoral dissertation, University of Utrecht (1971).
Zeng, X–N., et al., "An investigation of human apocrine gland secretion for axillary odor precursors," J. Chem. Ecol. 18:1039–1055 (1992).
Zeng, et al., "Analysis of characteristic odors from human male axillae," J. Chem. Ecol. 17:1469–1492 (1991).

*Primary Examiner*—Shelley A. Dodson
*Attorney, Agent, or Firm*—Woodcock Washburn Kurtz Mackiewicz & Norris

[57] ABSTRACT

It has now been found that cross-adaptation may occur between two structurally-similar compounds with qualitatively different odors. The perceived intensity of a malodor, for example, underarm sweat, may be decreased by cross-adaptation to at least one ester compound structurally similar to a component of such sweat. Such structurally similar compounds may be used in methods for decreasing the perceived intensity of a malodor such as sweat, in products designed to cover the characteristic odor of sweat, and in methods for covering malodor.

40 Claims, 5 Drawing Sheets

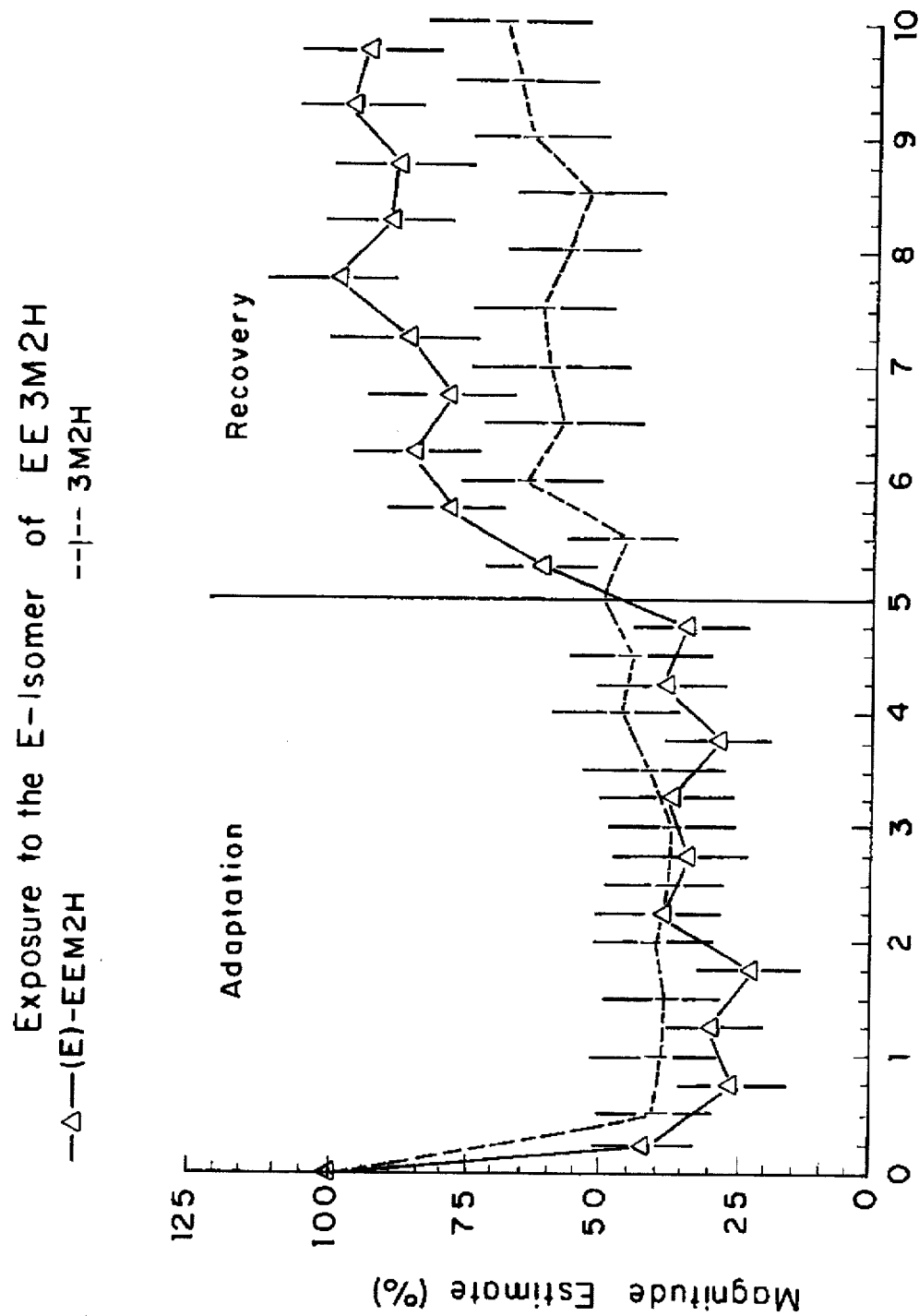

5,538,719

METHOD FOR REDUCING PERCEPTION OF HUMAN UNDERARM ODOR BY A PLEASANT SMELLING COMPOUND

GOVERNMENT RIGHTS

This invention was made with Government support under F32 DC00080 and R01 DC00298 awarded by the National Institutes of Health. The Government may have certain rights in this invention.

CROSS REFERENCE TO RELATED APPLICATIONS

This is a continuation-in-part of application Ser. No. 067,672, filed May 26, 1993.

FIELD OF THE INVENTION

The present invention relates to human olfactory adaptation, including human olfactory cross-adaptation, and more particularly, to methods and products for use in decreasing the perceived intensity of the odor of human secretions, especially sweat.

BACKGROUND OF THE INVENTION

Adaptation is the adjustment of an organism to its environment. The ability of an organism to adapt to sensory input, such as a smell, is well documented. Research has indicated that cross-adaptation may also occur. For example, an organism may cross-adapt to the sensory input of an odor. In such cross-adaptation, the perceived intensity of one odor may be decreased by subjecting or exposing the subject to a different odorant. Such cross adaptation may occur with perceptually similar odorants (perceptual analogs) and/or with structurally similar odorants (structural analogs).

Psychophysics can address structure-activity relationships in olfaction through the study of cross-adaptation; the decrease in sensitivity to one odor after exposure to a different odor. Cross-adaptation has been interpreted as a measure of the degree to which odors share common sensory channels (Engen, *The Perception of Odors*, Academic Press, New York (1982); Moncrieff, "Olfactory adaptation and odour likeness," *J. Physiol.*, 133:301–316 (1956)).

In comparing different odorants, a useful distinction can be made between perceptual and structural similarity. Perceptual analogs, i.e., compounds with similar smells, but not necessarily similar chemical structures, have been the focus of most research in the area of olfactory cross-adaptation. The evidence is clear that, despite great dissimilarities in chemical structure, perceptually similar odorants can produce cross-adaptation (Cain, "Odor intensity after self-adaptation and cross-adaptation," *Percept. Psychophys.*, 7:271–275 (1970); Engen & Lindstrom, "Cross-adaptation to the aliphatic alcohols," *Amer. J. Psych.*, 76:96–102 (1963); Moncrieff, supra (1956); Pierce, Wysocki & Aronov, "Mutual cross-adaptation of the volatile steroid androsterone and a non-steroid perceptual analog," *Chemical Senses* 18:245–56 (1993); Todrank, et al., "The effects of adaptation on the perception of similar and dissimilar odors," *Chem. Senses*, 16:467–482 (1991)). Further, cross-adaptation is more likely to occur with compounds that share all or most of their perceptual characteristics rather than a single trait (Moncrieff, supra (1956). Work with perceptual analogs suggests that structurally different odorants may stimulate the same sensory channels.

There is less available evidence concerning cross-adaptation among structural analogs; compounds with similar chemical structures, but having different odors. Cross-adaptation has been obtained in perceptually dissimilar compounds (Koster, "Adaptation and cross-adaptation in olfaction," Doctoral dissertation, University of Utrecht (1971)). For example, one study has reported significant cross-adaptation among a homologous series of aliphatic alcohols differing in carbon-chain length (Engen, supra (1963). Although significant cross-adaptation was observed, the degree of cross-adaptation did not vary in relation to the degree of physical similarity of the alcohols. Interpretation of the results was somewhat complicated in that several of the compounds in this study shared some perceptual similarities.

Another study reported cross-adaptation between the structurally similar, but perceptually distinct, n-propanol and n-pentanol (Cain, supra (1970)). Although these odorants were closely matched for intensity, the degree of cross-adaptation was asymmetric; pentanol more completely cross-adapted propanol than vice versa.

Although these studies suggest that structural similarity may be sufficient to yield significant cross-adaptation in perceptually different odorants in specific circumstances, the precise relationship remains obscure. The extent to which chemical structure similarity, in the absence of perceptual similarity, influences cross-adaptation is unknown.

Recently it was found that the (E) and (Z) isomers of 3-methyl-2-hexenoic acid (3M2H) are present in human secretions, especially male underarm sweat. More particularly, the (E)-isomer (E3M2H) has been identified as a major component in male underarm sweat (Zeng, X-N., et al., "An investigation of human apocrine gland secretion for axillary odor precursors," *J. Chem. Ecol.* 18:1039–1055 (1992); Zeng, et al., "Analysis of characteristic odors from human male axillae," *J. Chem. Ecol.* 17:1469–1492 (1991)). The (Z)-isomer (Z3M2H) is present at approximately 1/10 the concentration of the (E)-isomer.

SUMMARY OF THE INVENTION

It has now been found that significant cross-adaptation may occur between structurally-similar compounds with perceptually distinct odors. There is provided by the present invention, methods for reducing the perceived intensity of the odor of sweat, especially underarm sweat, by a subject, by cross-adapting the subject to an ester compound that is structurally similar to a component of such sweat. Such methods include methods for decreasing the perceived intensity of an odorant, such as the odor of human secretions, including sweat, comprising exposing a subject to at least one ester compound structurally similar to 3M2H.

There is further provided by the present invention products designed to cover the characteristic odor of sweat, especially underarm sweat. Such products include deodorants comprising at least one ester compound structurally similar to 3M2H and a suitable carrier.

Still further provided by the present invention are methods of covering malodor comprising providing to the locality of the malodor at least one ester compound structurally similar to 3M2H.

BRIEF DESCRIPTION OF THE DRAWINGS

FIG. 3 is a graph illustrating the mean magnitude estimates as a percentage of the initial estimates for 3M2H and the E-isomer of the ethyl ester of 3M2H following adaptation to the E-isomer.

DETAILED DESCRIPTION OF THE PREFERRED EMBODIMENTS

Figure 1A:
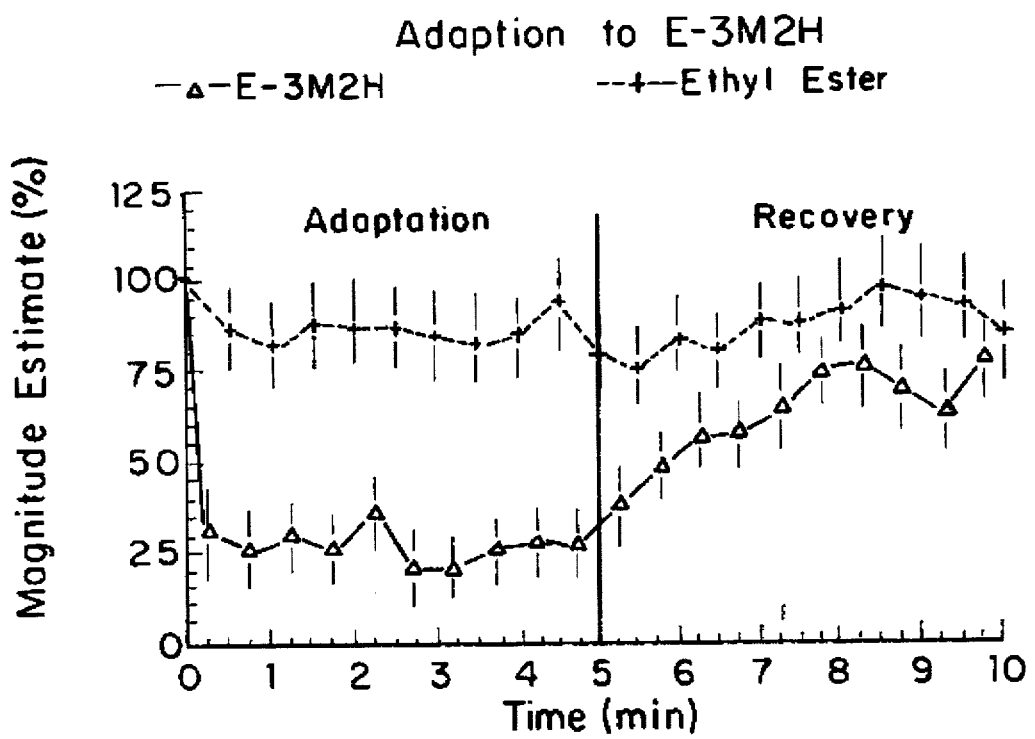
FIGS. 1a and 1b are graphs illustrating the mean magnitude estimates as a percentage of the initial estimates for 3M2H and the ethyl ester following adaptation to each compound.

It has now been found that significant cross-adaptation may occur between structurally-similar compounds with perceptually distinct odors. More particularly, it has now been found that ester compounds structurally similar to 3M2H can be used to decrease the perceived intensity of the odor of underarm sweat by a subject.

For example, the (E) and (Z) isomers of 3M2H, E3M2H and Z3M2H, respectively, are present in human secretions, especially male underarm sweat. The perceived intensity of the odor of underarm sweat may be decreased following adaptation to at least one ester compound structurally similar to 3M2H.

As used herein, ester compounds structurally similar to 3M2H include, but are not limited to, esters of 3M2H, such as methyl, ethyl, propyl, butyl, pentyl, hexyl and heptyl esters of 3M2H and its higher and lower homologues; esters of 3-methyl-2-octenoic acid (3M2O); and esters of 3-methyl-2-pentenoic acid (3M2P). Such ester compounds may include, for example, the separated ethyl ester isomers of 3M2H (EE3M2H) or its homologues, such as ethyl ester of (E)-3M2H (EEE3M2H) or ethyl ester of (Z)-3M2H (EEZ3M2H). In addition, methyl esters of 3M2H (ME3M2H), ethyl esters of 3M2O (EE3M2O), ethyl esters of 3M2P (EE3M2P), or any combination of the above may be used. Other ester compounds which are structurally similar to 3M2H will be readily identifiable by those skilled in the art.

One embodiment of this invention provides methods for reducing the perceived intensity of the odor of underarm sweat by a subject comprising the step of exposing the subject to at least one ester compound which is structurally similar to 3M2H.

Another embodiment of this invention provides methods for decreasing the perceived intensity of an odorant by a subject wherein said odorant comprises 3M2H. Such methods comprise exposing a subject to at least one ester compound which is structurally similar to 3M2H.

Another embodiment of this invention provides methods of covering malodor comprising providing to the locality of the malodor at least one ester compound which is structurally similar to 3M2H.

Another embodiment of this invention provides methods for decreasing the perceived intensity of human secretions by a subject comprising exposing the subject to at least one ester compound which is structurally similar to 3M2H.

Another embodiment of this invention provides deodorants comprising at least one ester compound which is structurally similar to 3M2H and a suitable carrier. As used herein, the term "deodorant" refers to but is not limited to an item or product that may be used to reduce the perceived intensity or cover malodor in a locality such as a bathroom, a clothes hamper, a locker room, a gymnasium, or on a surface. Such deodorants may be distributed or dispersed in, on, or around the area of the locality by methods known to those in the art, such as by spraying or by evaporation of a liquid or solid containing at least one ester compound which is structurally similar to 3M2H. Suitable carriers are known to those skilled in the art and vary depending upon the method of distribution or dispersement of the deodorant.

It has been found that cross-adaptation between structurally-similar compounds with qualitatively different odors is asymmetric. For example, as demonstrated in Example 1 (infra), while adaptation to EE3M2H significantly reduces the perceived intensity of the odor of 3M2H, adaptation to 3M2H does not significantly affect the perceived intensity of the odor of EE3M2H. There is, however, self-adaption; exposure to 3M2H reduces the perceived intensity of the odor of 3M2H. Such asymmetry may indicate that the sensory channel for 3M2H is a subset of the channel for EE3M2H. Adaptation to EE3M2H would therefore reduce the perceived intensity of itself and 3M2H, whereas exposure to 3M2H would induce self-adaptation, but not significant cross-adaptation to EE3M2H; inputs via independent sensory channels remain sufficient to maintain perceived intensity.

The data for recovery following adaptation is consistent with this suggestion of overlapping channels. It has previously been shown that when cross-adaptation occurred, a single sniff of an odorant every 15 seconds was sufficient to maintain adaptation and cross-adaptation (Pierce, et al., supra). Following cross-adaptation of 3M2H by EE3M2H, a single sniff of either 3M2H or the EE3M2H every 15 seconds is sufficient to maintain adaptation in the subset of the channel respondent to both EE3M2H and 3M2H. Consequently, there is no recovery of the perceived intensity of 3M2H following adaptation to EE3M2H. By comparison, estimates of the perceived intensity of EE3M2H significantly increase during the recovery period. In this instance, the independent subset of the channel respondent to EE3M2H is only being stimulated once every 30 seconds, allowing recovery. During the recovery seen in 3M2H following self-adaptation, the single sniff every 15 seconds should be sufficient to maintain adaptation. Yet, significant recovery is observed. Further, the 3M2H estimates during the last half of recovery following self-adaptation (overall mean of 74.2) were comparable to 3M2H estimates during the recovery period following cross-adaptation (overall mean of 73.6). Thus, in both conditions, estimates during recovery continued to be significantly reduced (by about one-fourth) relative to initial estimates.

EE3M2H and 3M2H differ since in the ester, the acidic hydrogen is replaced by an ethyl group. The ethyl esters and acid share a similar chemical exo-skeleton, but also differ substantially along several topographic and geometric dimensions. It may be that the physical differences in the shape and size of the hydrophobic part of the molecule contribute to the asymmetry in cross-adaptation. If the receptors are hydrophobic, then they should have a greater affinity for more hydrophobic compounds, such as ethyl esters, as opposed to acids. Thus, even following adaptation to the acid, the ethyl esters can occupy receptor sites by substituting for the acid. By contrast, acid molecules substitute less readily for the more hydrophobic ester molecules that may occupy receptor sites. Therefore, adaptation to the acid has little effect on the perception of the ethyl ester, whereas adaptation to the ethyl ester decreases the sensitivity to the acid because receptor sites remain occupied by the ethyl ester.

Although the precise relationship between chemical similarity and the extent of cross-adaptation is unknown, it is believed that the greater the structural similarity, the greater the extent of cross-adaptation.

In Example 2 (infra), 3M2H and EE3M2O, a homologue of 3M2H which possesses a fruity odor, were used. These compounds are less similar structurally than 3M2H and EE3M2H used in Example 1; the EE3M2O has two additional carbons in the acid portion of the molecule. The extent of cross-adaptation in Example 2, was less than that observed in Example 1.

Although overall changes in estimates for 3M2H following adaptation to EE3M2O fell short of statistical significance, there was evidence suggesting that some degree of cross-adaptation may have occurred. First, it is relevant that 3M2H estimates were reduced by 23% following adaptation to EE3M2O. This difference suggests that some sharing of perceptual channels may occur. Second, recovery data provide another source of evidence that some cross-adaptation may have occurred between 3M2H and EE3M2O. 3M2H estimates continued to decrease during the recovery period, when odorants that appear to stimulate independent channels typically show increases in relative intensity (Pierce & Wysocki, supra (1992)). There may be partial overlap in the sensory channels stimulated by EE3M2O and 3M2H. These findings have practical implications. That EE3M2O reduced perception of 3M2H indicates that it may be used to control or cover malodor, or to decrease the perceived intensity of the odor of underarm sweat.

In Example 3 (infra), 3M2H and the ethyl esters of 3M2P (EE3M2P) were used. There was less interaction between 3M2H and EE3M2P; adaptation to this ethyl ester reduced 3M2H estimates by about fourteen percent and there was full recovery following exposure to EE3M2P.

Similar to EE3M2O, although overall changes in estimates for 3M2H following adaptation to EE3M2P fell short of statistical significance, there is evidence that some cross-adaptation may have occurred. These findings have practical implications. That EE3M2P reduced perception of 3M2H indicates that it also may be used to control or cover malodor, or the decrease the perceived intensity of the odor of underarm sweat.

In Example 4 (infra), the effectiveness of individual ethyl ester isomers EEE3M2H (ethyl ester of (E)-3M2H) and EEZ3M2H (ethyl ester of (Z)-3M2H) at reducing the perception of 3M2H was assessed. Exposure to EEE3M2H rapidly and significantly reduced the perception of 3M2H, and the intensity of 3M2H remained depressed following removal of the adapting stimulus. Exposure to EEZ3M2H also significantly reduced the perception of 3M2H but was less effective than EEE3M2H. That the purified EEE3M2H appears to be the most effective cross-adapting agent for 3M2H suggests that E-isomers of ethyl esters not only of 3M2H, but also of higher and lower homologues of 3M2H such as 3M2O and 3M2P, may be more efficacious in their ability to cross-adapt 3M2H than an E-, Z-isomer mixture.

In Example 5 (infra), the effectiveness of methyl esters of 3M2H (ME3M2H) at reducing the perception of 3M2H was assessed. Exposure to ME3M2H significantly reduced the perception of 3M2H. That ME3M2H produces significant cross-adaptation to 3M2H suggests that chemically similar compounds in the same family would cross-adapt 3M2H. For example, other esters of 3M2H, such as propyl, butyl, pentyl, hexyl and heptyl esters, may be effective in this regard.

The finding that structural similarity may affect the extent of cross-adaptation differs from the results reported by Engen (1963) who reported that cross-adaptation among a homologous series of aliphatic alcohols differing in carbon-chain length did not vary in relation to the degree of physical similarity of the alcohols. The perceptual similarities in the series of alcohols used by Engen (1963) may have confounded the effects of structural similarity. By contrast, the compounds used in the examples herein did not share perceptual characteristics. For example, 3M2H has the odor of underarm sweat, and the ethyl esters have fruity odors.

In addition, Engen measured threshold levels and the number of correct identifications, whereas the present study focused on magnitude estimation of supra-threshold stimuli.

Having demonstrated the efficacy of the ethyl and methyl esters of 3M2H in reducing the perception (via cross-adaptation) of malodor, molecular modeling of the esters and the acids was performed to examine the correspondence between structural parameters of the compounds tested and cross-adaptation. This analysis revealed that the acids and esters had virtually identical charge distribution; however, the shape and size of the hydrophobic part of the molecules appear to be more critical for cross-adaption. While these parameters are most identical for EEE3M2H and 3M2H, which displayed the strongest cross-adaptation, they are less so for EEZ3M2H, EE3M2O, EE3M2P, as well as the methyl propyl, butyl and remaining ester compounds structurally similar to 3M2H. As such, the common olfactory receptors for the esters of 3M2H and the acid should be hydrophobic. The fact that esters are more hydrophobic than acids is predictive that all ester compounds structurally similar to 3M2H will have some efficacy in cross-adapting. Further, these esters may have efficacy in cross-adapting a variety of malodors which consist of mixtures of volatile organic acids.

The current findings have practical implications with respect to the control of malodor, e.g., the odor of underarm sweat. The effectiveness of ester compounds structurally similar to 3M2H in decreasing the perception of 3M2H, a principal component of the odor of human underarm sweat, is demonstrated. As such, ester compounds structurally similar to 3M2H may be used in combination with a suitable carrier to form a deodorant.

Further practical implications include the utilization of ester compounds structurally similar to 3M2H in decreasing the perceived intensity of the smell of human secretions or an odorant, especially underarm sweat. In such methods, the perceived intensity of the smell of sweat, especially underarm sweat, is decreased by first exposing or cross-adapting the subject to at least one ester compound structurally similar to 3M2H.

In certain embodiments of the present invention, the at least one ester compound structurally similar to 3M2H comprises an ethyl ester of 3M2H, such as ethyl ester of (E)-3M2H or ethyl ester of (Z)-3M2H. In other embodiments, the at least one ester compound structurally similar to 3M2H comprises an ethyl ester of 3M2O. In other embodiments, the at least one ester compound structurally similar to 3M2H comprises an ethyl ester of 3M2P. In other embodiments, the at least one ester compound structurally similar to 3M2H comprises a methyl ester of 3M2H. Ester compounds structurally similar to 3M2H further comprise other esters of 3M2H, such as propyl, butyl, pentyl, hexyl and heptyl esters of 3M2H.

In still other embodiments, the at least one ester compound structurally similar to 3M2H comprises a mixture of ester compounds structurally similar to 3M2H, such as a mixture of ethyl ester of (E)-3M2H and ethyl ester of (Z)-3M2H. In certain preferred embodiments, the mixture comprises EEE3M2H and EEZ3M2H in a 3:1 ratio. In other embodiments, the mixture is in a liquid solution comprising about 5–8 mM of EEE3M2H and EEZ3M2H per milliliter of liquid.

Variations and modifications of the aforementioned can, of course, be made without departing from the spirit and scope of the invention as disclosed herein, and those skilled in the art will recognize multiple utilizations of the present invention that are within the scope of this disclosure.

TABLE OF ABBREVIATIONS

Abbreviation: Compound
3M2H: 3-methyl-2-hexenoic acid
3M2O: 3-methyl-2-octenoic acid
3M2P: 3-methyl-2-pentenoic acid
(E)-3M2H: (E)-3-methyl-2-hexenoic acid
(Z)-3M2H: (Z)-3-methyl-2-hexenoic acid
EE3M2H: ethyl esters of 3-methyl-2-hexenoic acid
ME3M2H: methyl esters of 3-methyl-2-hexenoic acid
EEE3M2H: ethyl ester of (E)-3-methyl-2-hexenoic acid
EEZ3M2H: ethyl ester of (Z)-3-methyl-2-hexenoic acid

EXAMPLES

Materials and Methods for Examples 1–3:

A synthetic mixture of E3M2H and Z3M2H was formulated in the 10:1 ratio found in the naturally occurring underarm secretions (Zeng et al., supra (1992)).

To address the role of structural similarity in producing cross-adaptation, three homologous ethyl esters were selected. These were EE3M2H, EE3M2O, and EE3M2P. The ethyl esters of organic acids are structurally similar to the corresponding acids with the acid hydrogen being replaced by an $CH_2CH_3$ (ethyl) moiety. In contrast to the volatile organic acids, the ethyl esters of these compounds are pleasant smelling and quite often used as fruity flavors in food and candies. The ethyl esters used were synthesized and used in a 3:1 ratio of (E):(Z) isomers.

Example 1

In Example 1, cross-adaptation was assessed for 3M2H and EE3M2H.

Subjects. Twelve subjects (six male and six female; mean age of 30.0) were recruited. Since there is evidence to suggest specific anosmias for both isomers of 3M2H, all subjects were screened for sensitivity to the odorants used in the study.

Stimuli. Two odorants, a 10:1 (E)- to (Z)-3M2H mixture and a 3:1 mixture of their ethyl esters, were used. Each odorant was synthesized and purified by column chromatography in a manner described previously (Zeng et al., supra (1991)). Odorants were diluted in odorless, light, white, mineral oil and presented in 270 ml, polypropylene squeeze-bottles with plastic, flip-top caps. Each bottle contained 10 ml of odorant. Blanks consisted of 10 ml of mineral oil without odorant in squeeze-bottles.

A 12-step binary dilution series was prepared for each odorant. Initially, 20 mg of each odorant was diluted in 20 ml of odorless, light, white, mineral oil to yield a 1 mg/ml (0.1% w/v) solution with molar concentrations of 7.81 mM/ml for 3M2H and 6.32 mM/ml of EE3M2H. The dilution scheme for each odorant was thus identical, ranging from the initial concentration of $1.0 \times 10^{-1}\%$ w/v (step 12) to $4.88 \times 10^{-5}\%$ w/v (step 1; the weakest concentration).

Procedure. Subjects were tested in two 30-minute sessions separated by at least 24 hr. The adapting odorant, either 3M2H or its ethyl ester, was counterbalanced across sessions. A forced-choice, staircase procedure was used at the beginning of each session to equate intensities. Each trial consisted of a step-10 concentration of 3M2H and an alternating concentration of the ethyl ester (starting at step 8). Subjects were instructed to identify the more intense of the two bottles. Each pair of stimuli was presented twice, with trials separated by one minute. If the subject selected the ethyl ester on each of the two trials, the subsequent trial used the next weaker concentration of that odorant. Similarly, if 3M2H was selected twice, the next stronger concentration of the ethyl ester was used. The concentration of ethyl ester at which subjects failed to identify the same stimulus as stronger on two consecutive trials was selected as the concentration most similar in intensity to step-10 of 3M2H. The adapting stimuli were the concentrations two binary steps higher than the intensity-matched test stimuli.

A two-minute rest was imposed following perceptual matching, then, using magnitude estimation, subjects rated the intensities of step 10 of 3M2H and the intensity-matched ethyl ester stimulus. Subjects rated each of these two stimuli twice. If the means of the magnitude estimates of each odor were dissimilar (greater than 20% discrepancy), the matching procedure was repeated. In this manner, initial magnitude estimates ensured that the two stimuli were perceptually equivalent for that subject.

After making the initial magnitude estimates, subjects began to sniff repeatedly the adapting stimulus (either step 12 3M2H or the concentration two steps above the intensity-matched ethyl ester). Every 15 seconds during this adaptation period, subjects sniffed and rated a test stimulus between sniffs of the adapting stimulus. The test stimulus, either 3M2H or the ethyl ester, alternated on sequential trials so that subjects made a total of 20 ratings (10 3M2H, 10 ethyl ester) during the 5 min adaptation period. Following these ratings, the adapting stimulus was removed and subjects continued to rate test stimuli every 15 seconds during a 5 min post-adaptation period. Subjects thus made a total of 20 ratings during this recovery period.

Results

Figure 1B:
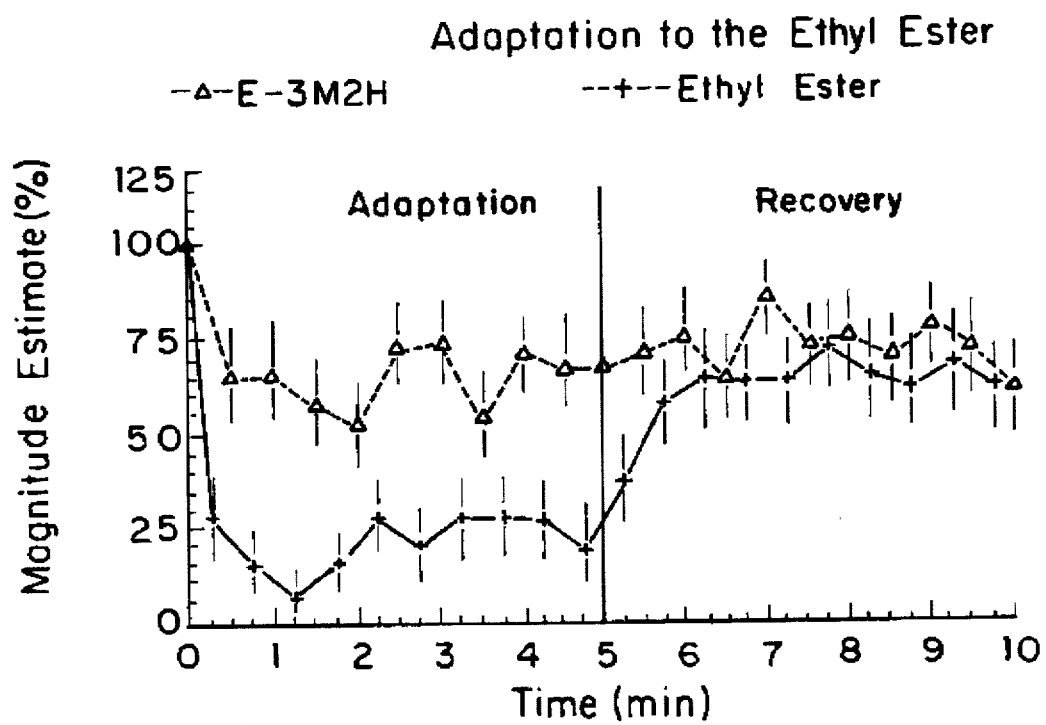

Self-Adaptation: Each magnitude estimate was converted to a percentage of the initial magnitude estimate for that odorant; the resulting percentages are presented in FIGS. 1a and 1b. Repeated measures ANOVAs (analysis of variance), conducted after each estimate was first subtracted from 100, assessed whether estimates were significantly different from the initial estimates (100%), with significance levels set at $p<0.01$ because multiple F-tests were performed. Each odorant showed significant self-adaptation (3M2H: $F(1,11)=106.79$, $p<0.001$ ; EE3M2H: $F(1,11)=98.54$, $p<0.001$). There was no significant effect of trials, as self-adaptation occurred quickly and estimates remained depressed for the duration of the adaptation period. Thus, estimates for ethyl ester during self-adaptation were reduced to 28.3% of initial estimates within 15 seconds, and did not vary significantly through the adaptation period (overall mean estimate=21.8% of initial estimates; comparison across trials: F (9,99)=1.76; p>0.05). Similarly, estimates for 3M2H during self-adaptation were 31.3% of initial estimates within 15 seconds, and did not change significantly during adaptation (overall mean estimate=27.7%; comparison across trials: F (9,99)=0.78, p>0.60). Following self-adaptation, each odorant displayed significant recovery, albeit not to baseline levels: Estimates during recovery were significantly greater than estimates during self-adaptation (Ethyl ester: Overall mean=62.3%; F (1,11)=23.57, p<0.001; 3M2H: Overall mean=64.4%; F (1,11)=42.03, p<0.001), but still significantly lower than the initial estimates (Ethyl ester: F (1,11)=8.86; p<0.01; 3M2H: F (1,11)=12.69; p<0.004).

Cross-adaptation: Cross-adaptation was noted only in one direction. Adaptation to 3M2H did not significantly affect estimates of the intensity of the ethyl ester (overall mean estimate=86.3%; F (1,11)=2.54, p>0.10), but adaptation to the ethyl ester resulted in significantly reduced estimates of intensity for 3M2H (overall mean estimate=64.9% of initial estimates; F (1,11)=22.20; p<0.001). As with self-adaptation, there was no significant effect of trials; 3M2H cross-adapted quickly (estimates were reduced to 65.0% of initial estimates within 30 seconds) and remained cross-adapted for the duration of the adaptation period (comparison across trials: F (9,99)=1.73; p>0.05). Further, the intensity of 3M2H remained depressed following removal of the adapting stimulus: During recovery, its intensity did not differ significantly from estimates made during adaptation (F (1,11)=1.15, p>0.30) and did not change significantly across the recovery period (F (9,99)=1.88, p>0.05). The reduction in perceived intensity of 3M2H noted during cross-adaptation was significantly less than that seen during self-adaptation to 3M2H (F (1,11)=30.12; p<0.001).

Example 2

Subjects. Twelve subjects (six males and six females; mean age of 25.8) were recruited. Five of these subjects had served as participants in Example 1. All subjects were screened for sensitivity to the odorants used in the study.

Stimuli. Two odorants, 3M2H and the ethyl ester of 3M2O (EE3M2O), were used. Both compounds were synthesized in a manner described previously (Zeng et al., supra (1991)). Odorants were diluted and presented in the same manner as in Example 1. Dilution schemes were likewise similar, ranging from $1.0 \times 10^{-1}\%$ w/v (step 12; 7.81 mM/ml of 3M2H, 5.37 mM/ml of EE3M2O) to $4.88 \times 10^{-5}\%$ w/v (step 1).

Procedure. The adapting odorants were step 12 of each odorant and were counterbalanced across sessions. The test odorants were step 10 of the adapting odorant and the concentration of the other odorant judged to be most similar in intensity, using the matching procedure described in Example 1. Procedures were otherwise similar to those of Example 1.

Results

Figure 2A:
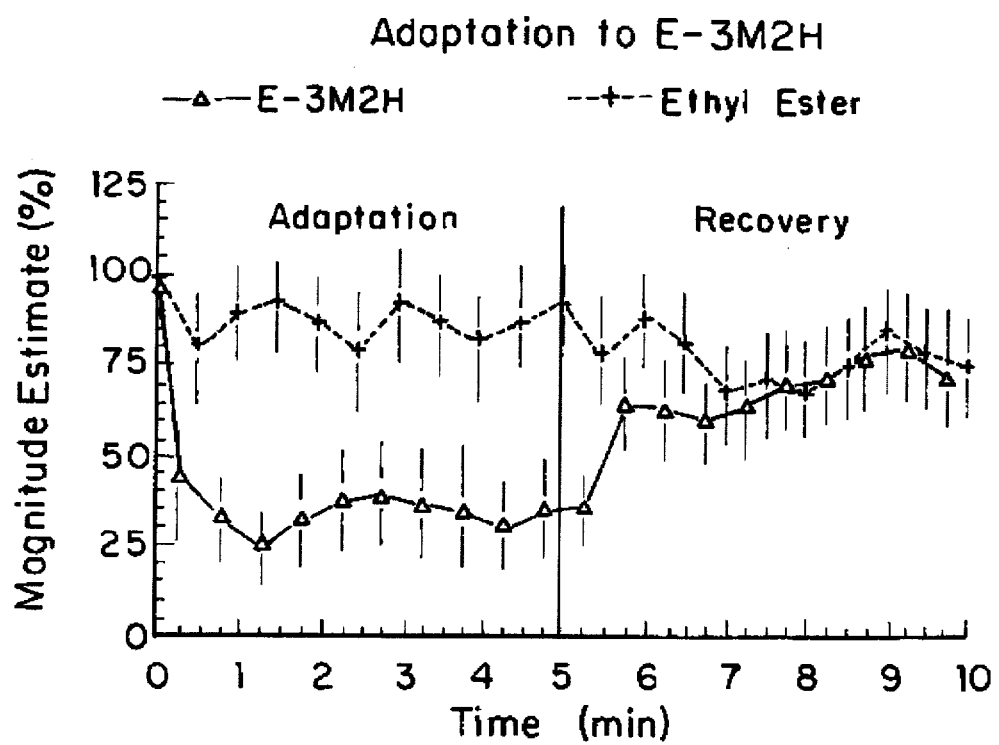
FIGS. 2a and 2b are graphs illustrating the mean magnitude estimates as a percentage of the initial estimates for 3M2H and the ethyl esters of E-Z-3M2O (E-Z-3-methyl-2-octenoic acid) following adaptation to each compound.
Figure 2B:
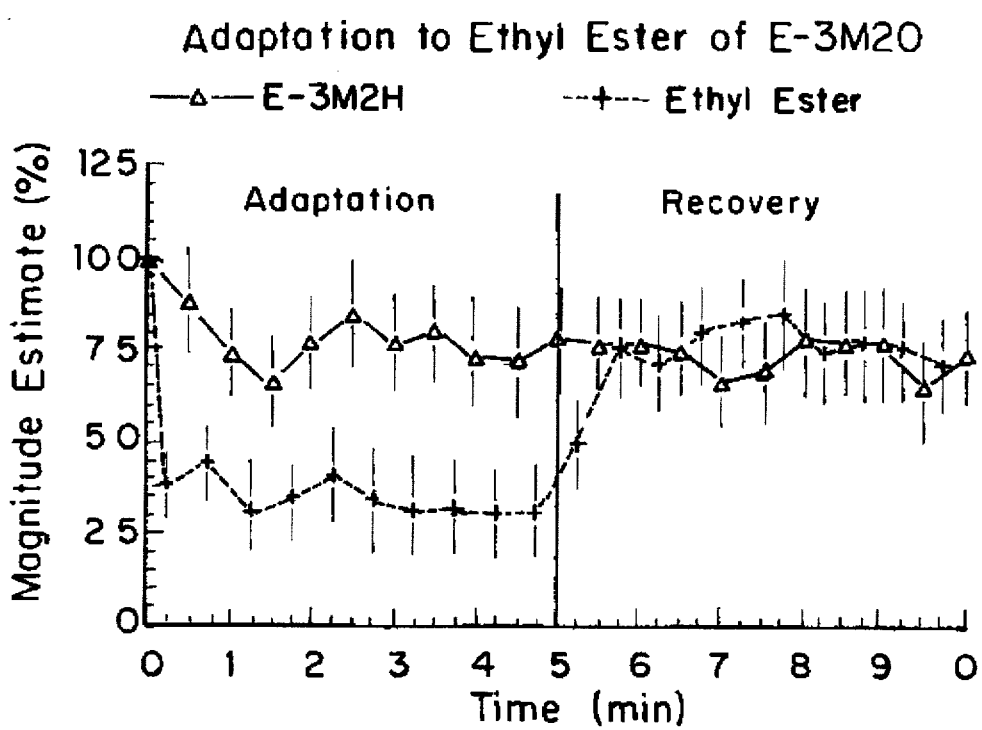

Self-Adaptation: Each magnitude estimate was converted to a percentage of the initial magnitude estimate for that odorant; the resulting percentages are presented in FIGS. 2a and 2b. Each odorant showed significant self-adaptation (3M2H: F (1,11)=53.68, p<0.001; EE3M2O: F (1,11)=62.36, p<0.001). For each odorant, self-adaptation occurred quickly and continued for the duration of the adaptation period (3M2H: overall mean estimate=35.0% of initial estimates; comparison across trials while adapted: F (9,99)=0.55, p>0.80; EE3M2O: overall mean estimate= 34.9% of initial estimates; comparison across trials while adapted: F (9,99)=0.55; p>0.80). Following adaptation, significant recovery was noted for the ethyl ester; estimates during recovery were significantly greater than estimates during adaptation F (1,11)=18.71, p<0.001) and did not differ significantly from initial estimates (F (1,11)=5.73; p>0.03). Estimates for 3M2H likewise displayed significant recovery (F (9,99)=30.25; p<0.001), but were still significantly lower than initial estimates (F (1,11)=13.25; p<0.004).

Cross-Adaptation: No significant cross-adaptation was noted in either session. Adaptation to 3M2H did not significantly affect EE3M2O estimates of intensity during adaptation (overall mean estimate=86.3%; F (1,11)=1.70, p>0.20). Estimates during recovery were similarly unaffected; they did not differ from initial estimates (F (1,11)= 7.06; p>0.01) nor from estimates made during adaptation (F (1,11)=4.34, p>0.05). Adaptation to EE3M2O resulted in reduced estimates for 3M2H, but this reduction fell short of the 0.01 level set for statistical significance (overall mean estimate=77.0% of initial estimates; F (1,11)=6.23; p>0.02). However, the general decrease in 3M2H estimates during adaptation to EE3M2O continued following removal of the adapting stimulus. Thus, 3M2H estimates during recovery differed significantly from initial estimates (F (1,11)=7.72, p<0.01), and did not differ significantly from estimates made during adaptation (F (1,11)=0.24; p>0.60). Overall, 3M2H estimates during cross-adaptation were significantly higher than estimates made during self-adaptation (F (1,11)=16.55; p<0.002).

Example 3

Subjects. Twelve subjects (six males and six females; mean age of 26.7) were recruited. Eight of these subjects had served as participants in either Example 1 or Example 2. All subjects were screened for sensitivity to the odorants used in the experiment.

Stimuli. Two odorants, 3M2H and the ethyl ester of 3M2P (EE3M2P), were used. Both compounds were synthesized in a manner described previously (Zeng et al., supra (1991)). Odorants were diluted and presented in the same manner as in Examples 1 and 2. Dilution schemes were likewise similar, ranging from $1.0 \times 10^{-1}\%$ w/v (step 12; 7.81 mM/ml of 3M2H, 6.93 mM/ml of EE3M2P) to $4.88 \times 10^{-5}\%$ w/v (step 1).

Procedure. The adapting odorants were step 12 of each odorant and were counterbalanced across sessions. The test odorants were step 10 of the adapting odorant and the concentration of the other odorant judged to be most similar in intensity, using the matching procedure described above. Procedures were otherwise similar to those described above.

Results

No significant cross-adaptation was noted between 3M2H and EE3M2P. Exposure to 3M2H did not affect the perception to EE3M2P. Similarly, exposure to EE3M2P did not affect the perception to 3M2H. Further, estimates during the recovery phase did not differ significantly from initial estimates for either odorant.

Example 4

Individual ethyl ester isomers (E and Z) of 3M2H were isolated and purified in order to assess their effectiveness at reducing the perception of 3M2H. These are referred to as EEE3M2H and EEZ3M2H, respectively.

Synthesis and Separation: Ethyl-3-methyl-2-hexenoic Esters

A mixture of the E and Z isomers was synthesized via Wittig methodology in the following manner: To a stirred slurry of 4.48 g (0.112) NaH (60% in mineral oil) in 100 ml anhydrous toluene under $N_2$ blanket was added, dropwise, 22.0 ml (0.111 mol) triethyl phosphonoacetate. The resulting betaine was allowed to form at room temperature over 30 minutes. To this reactive intermediate, 11.8 ml (0.11 mole) 2-pentanone was added while the reaction mixture was heated to 40° C. The reaction mixture was stirred for 16 h to yield a viscous, biphasic product. GC analysis indicated the formation of the esters: STABILWAX column (30 M×0.53 mm i.d.); 64° C. isothermal: Z $R_F$: 15 min.; E $R_F$: 20 min.) in 1:3 ratio. The reaction mixture was poured into ice water and extracted with three, 100 ml portions of ether, dried over $Na_2SO_4$, filtered and carefully concentrated to yield 20.3 g of a clear, fruity smelling volatile oil. Flash chromatography (1% Ether in Hexane) was employed to remove residual toluene, leaving 15.5 g (89.6%) of the ethyl ester mixture. GC/MS analysis of the ester mixture confirmed the 1:3 ratio of Z:E isomers and the presence of an exo double bond rearrangement (Ethyl-3-methylidine-hexanoic ester) in 1.1% yield. No $\beta$, $\gamma$ double bond migration was observed.

Separation of the E and Z ethyl esters was accomplished via preparative HPLC (Zorbax Sil 9.4 mm×25 cm column (8 μm); mobile phase: 1% ether in hexane; 10 ml/min (15 mPa); Varian RI-3 refractive index detector ($500×10^{-6}$ RI/FS sensitivity)}. Injection size was 400 μl of a 20% solution of the esters in mobile phase. Capacity factors for the Z and E esters were: $k'_z$=3.33 and $k'_e$=4.33, ($\alpha$=1.3). GC/MS of the (E)-Ethyl-3-methyl-2-hexenoate indicated 99.4% of the compound to be the E,SZ form, and 0.6% to be the E,SE form of the ester. GC/MS of the (Z)-Ethyl-3-methyl-2-hexenoate showed 93.4% to be the Z,SZ form, with the closely eluting exo compound, ethyl-3-methylidine-hexanoic ester, ($k'_{EXO}$=3.5; $\alpha$=1.05) comprising 3.4% of the sample. The remaining 3.2% exhibited M+ peaks at 128, indicating hydrolysis of the ester to the acid.

Subjects. Twelve subjects (six male and six female; mean age of 25.0 years) were tested in each of two sessions comparing 3M2H with the individual (E) and (Z) isomers of EE3M2H.

Stimuli. The odorants used were a 10:1 (E)- to (Z)-3M2H mixture and the individual (E) and (Z) isomers of EE3M2H. Each odorant was synthesized and presented in the manner described previously. A 12-step binary dilution series was prepared for each odorant, ranging from the strongest concentration of $1.0×10^{-1}$% w/v (step 12) to $4.88×10^{-5}$% w/v (step 1; the weakest concentration).

Procedure. The procedure was similar to that described previously. Twelve subjects participated in each of two sessions. The adapting odorants were the (E)-isomer of EE3M2H in one session and the (Z)-isomer of EE3M2H in the other session.

Results

Self-Adaptation

Figure 4:
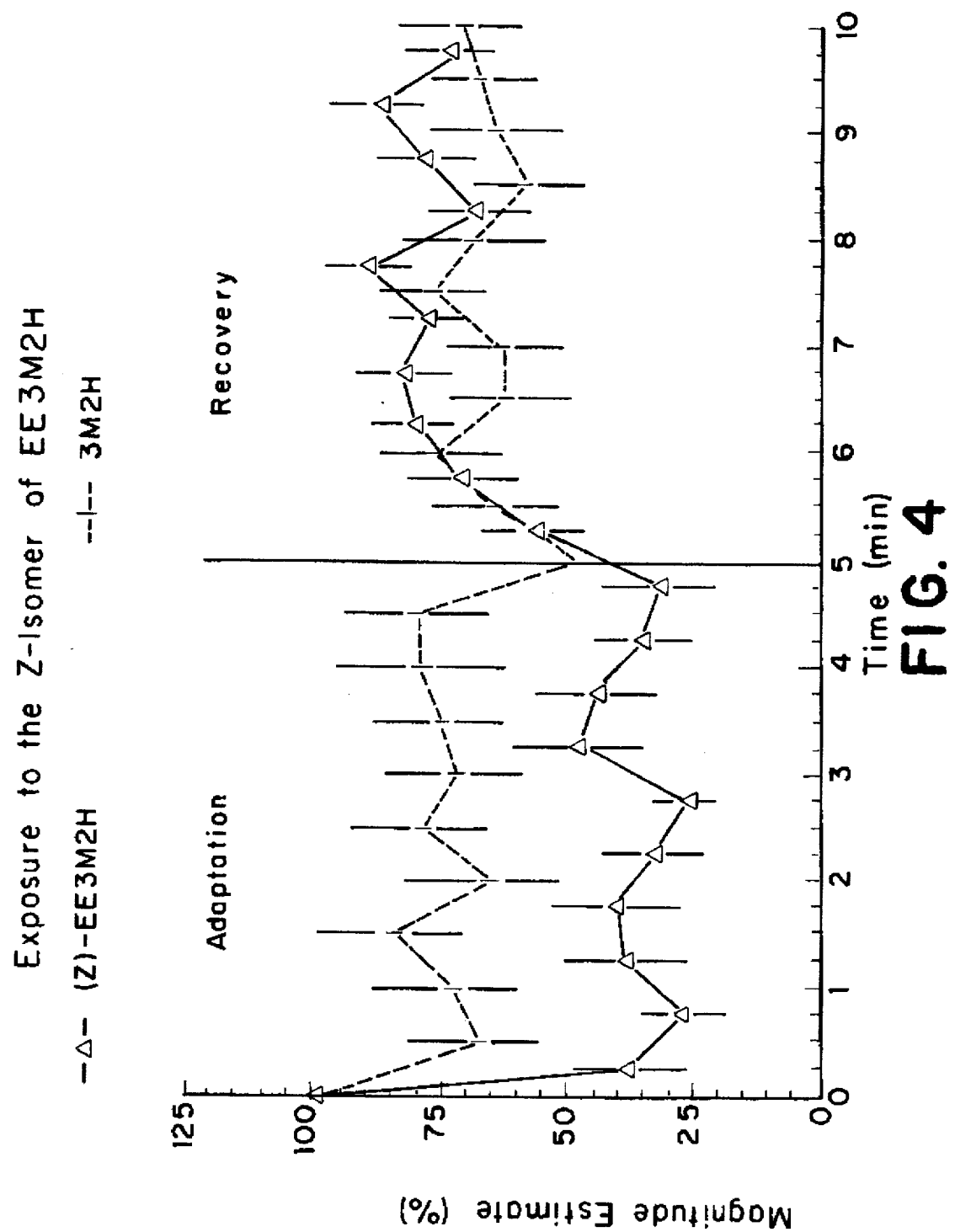
FIG. 4 is a graph illustrating the mean magnitude estimates as a percentage of the initial estimates for 3M2H and the Z-isomer of the ethyl ester of 3M2H following adaptation to the Z-isomer.

For each odorant, self-adaptation occurred quickly and estimates remained depressed for the duration of the adaptation period (see FIGS. 3 and 4).

Cross-adaptation

Exposure to the (E)-isomer of EE3M2H rapidly and significantly reduced the perception of 3M2H (E $(1,11)$= 47.28; p<0.001). On average, the perception of the intensity of 3M2H was reduced by 58.1% (see FIG. 3), a reduction greater than that observed following adaptation to the 3:1 (E:Z) isomer mix of EE3M2H (35.1%). In addition, use of the pure E-isomer caused adaptation to occur within the first 30 seconds of exposure (the "first sniff"). In contrast, the strongest effect of the 3:1 isomer mixture occurred only after 2 mins of exposure.

The intensity of 3M2H remained depressed following removal of the (E)-isomer of EE3M2H as the adapting stimulus (an average reduction of 40.2% compared to initial estimates). Thus, the estimates made during recovery continued to differ significantly from estimates made prior to adaptation (F $(1,11)$=20.05, p<0.001).

Exposure to EEZ3M2H was less effective in reducing the perception of 3M2H. On average, the perception of the intensity of 3M2H was reduced by 27.9% following adaptation to EEZ3M2H. While this reduction is still statistically significant (F $(1,11)$=5.27, <0.05) it is less effective than E-isomer. However, the intensity of 3M2H continued to lessen following removal of the EEZ3M2H adapting stimulus. Thus, estimates made during the recovery period were significantly different from the estimates made prior to adaptation (F $(1,11)$=11.46, p<0.006). On average, the perception of 3M2H during the recovery period was reduced 33.1% relative to initial estimates.

Example 5

Synthesis of the methyl esters was performed using 1 g of a 3:1 mixture of the (E,Z)-3-methyl-2-hexenoic acids. These were dissolved in 25 mls of Nanograde methanol to which was added 0.5 ml of concentrated $H_2SO_4$. This mixture was refluxed for 1.5 hrs. The reaction mixture was poured into a 50/50 mixture (2 phases) of doubly distilled $H_2O$ and Nanograde $CH_2Cl_2$ and cooled to -5° C. The solution was slowly neutralized. The remaining 3-methyl-2-hexenoic acid (3M2H) was separated from the methyl ester by passing the $CH_2Cl_2$ layer (above) through a column of silica gel which contained several drops of $NH_4OH$ added to the top. The $CH_2Cl_2$ was removed by distillation to yield a solvent-free mixture of esters.

Subjects. Twelve subjects (five male and seven female; mean age of 25.3 years) were tested in each of two sessions comparing 3M2H with the methyl ester of 3M2H (ME3M2H).

Stimuli. The odorants used were a 10:1 (E)- to (Z)-3M2H mixture and a mixture of the methyl esters of 3M2H, synthesized as described above. A 12-step binary dilution series was prepared for each odorant, ranging from the strongest concentration of $1.0×10_{-1}$% w/v (step 12) to $4.88×10^{-5}$% w/v (step 1; the weakest concentration).

Procedure. The procedure was similar to that described previously. Subjects participated in each of two sessions. The adapting odorants were the methyl ester of 3M2H in one session and 3M2H in the other session.

Results

Self-Adaptation

Figure 5:
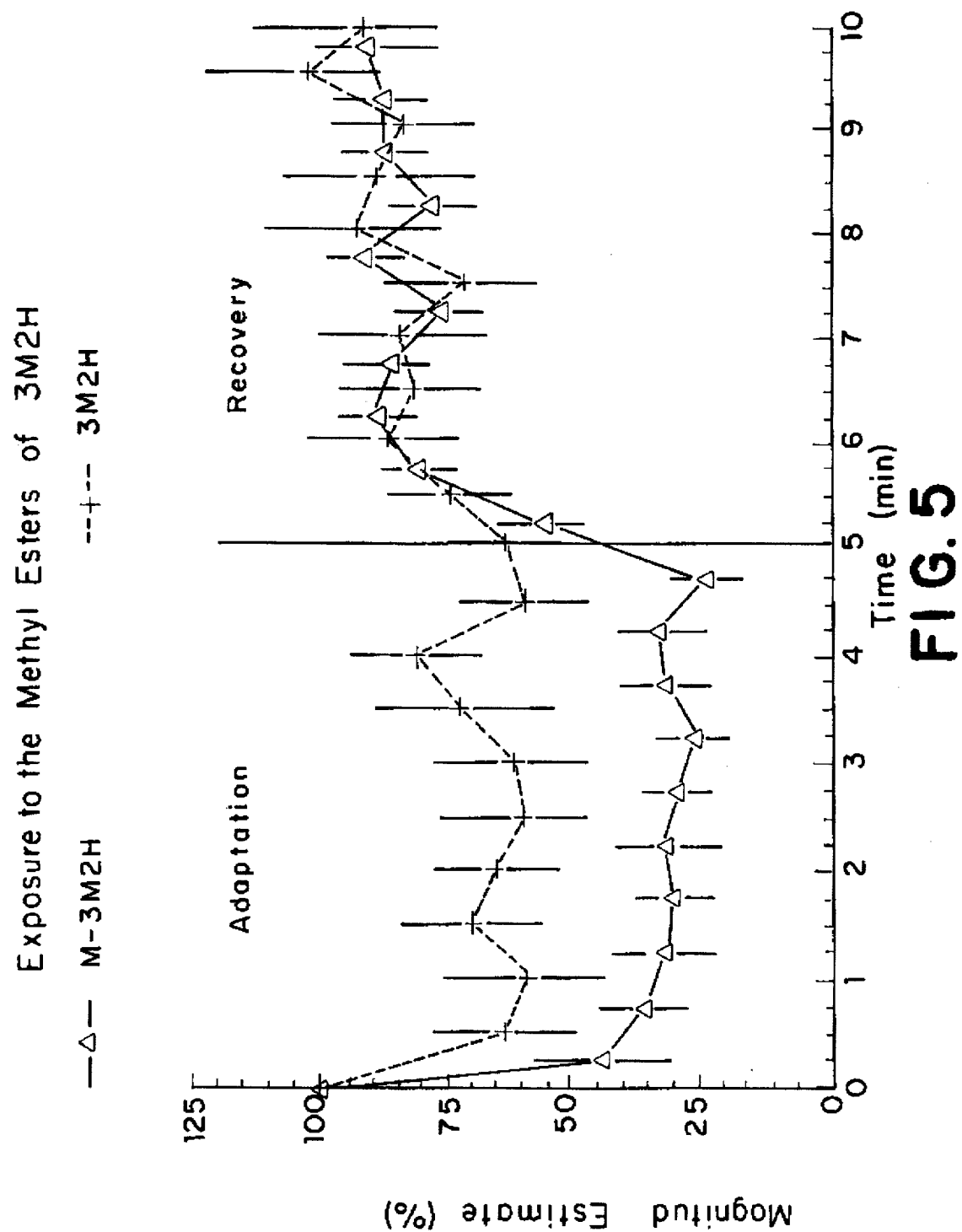
FIG. 5 is a graph illustrating the mean magnitude estimates as a percentage of the initial estimates for 3M2H and the methyl ethers of 3M2H following adaptation to the methyl ethers of 3M2H.

For each odorant, self-adaptation occurred quickly and estimates remained depressed for the duration of the adaptation period (see FIG. 5).

Cross-adaptation

Exposure to ME3M2H significantly reduced the perception of 3M2H (F (1,11)=7.80; p<0.02). On average, the perception of the intensity of 3M2H was reduced by 34.3% (see FIG. 5), a reduction comparable to that produced by the 3:1 mixture of E:Z ethyl esters of 3M2H on 3M2H (35.1%). This reduction in intensity did not continue during the recovery period; the intensity of 3M2H increased significantly following removal of ME3M2H as the adapting stimulus. During recovery, estimates of its intensity did not differ significantly from estimates made prior to adaptation (F (1,11)=1.10, p>0.30).

Cross-adaptation was asymmetrical; adaptation to 3M2H did not significantly reduce the perception of ME3M2H (average reduction of 20.1%; F (1,11)=5.69, p>0.03). Estimates made during the recovery period were not significantly different from those made prior to adaptation (F (1,11)=2.37, p>0.30).

We claim:

1. A method for decreasing the perceived intensity of a body malodor by a subject comprising the step of exposing said subject to at least one ester compound selected from the group comprising ethyl esters of 3-methyl-2-hexenoic acid, ethyl esters of 3-methyl-2-octenoic acid, ethyl esters of 3-methyl-2-pentenoic acid, and methyl esters of 3-methyl-2-hexenoic acid.

2. The method of claim 1 wherein said ethyl esters of 3-methyl-2-hexenoic acid are selected from the group comprising ethyl ester of (E)-3-methyl-2-hexenoic acid and ethyl ester of (Z)-3-methyl-2-hexenoic acid.

3. The method of claim 1 wherein said at least one ester compound comprises a mixture of ethyl ester of (E)-3-methyl-2-hexenoic acid and ethyl ester of (Z)-3-methyl-2-hexenoic acid.

4. The method of claim 3 wherein said mixture comprises ethyl ester of (E)-3-methyl-2-hexenoic acid and ethyl ester of (Z)-3-methyl-2-hexenoic acid in a 3:1 ratio.

5. The method of claim 4 wherein said mixture is in a liquid solution comprising 5–8 mM of the mixture of ethyl ester of (E)-3-methyl-2-hexenoic acid and ethyl ester of (Z)-3-methyl-2-hexenoic acid per milliliter of liquid.

6. The method of claim 1 wherein said at least one ester compound comprises ethyl ester of (E)-3-methyl-2-hexenoic acid.

7. The method of claim 1 wherein said at least one ester compound comprises ethyl ester of (Z)-3-methyl-2-hexenoic acid.

8. The method of claim 1 wherein said at least one ester compound comprises methyl ester of 3-methyl-2-hexenoic acid.

9. The method of claim 1 wherein said at least one ester compound comprises ethyl ester of 3-methyl-2-octenoic acid.

10. The method of claim 1 wherein said at least one ester compound comprises ethyl ester of 3-methyl-2-pentenoic acid.

11. A method for decreasing the perceived intensity of the odor of 3-methyl-2-hexenoic acid by a subject comprising the step of exposing said subject to at least one ester compound selected from the group comprising ethyl esters of 3-methyl-2-hexenoic acid, ethyl esters of 3-methyl-2-octenoic acid, ethyl esters of 3-methyl-2-pentenoic acid, and methyl esters of 3-methyl-2-hexenoic acid.

12. The method of claim 11 wherein said ethyl esters of 3-methyl-2-hexenoic acid are selected from the group comprising ethyl ester of (E)-3-methyl-2-hexenoic acid and ethyl ester of (Z)-3-methyl-2-hexenoic acid.

13. The method of claim 11 wherein said at least one ester compound comprises a mixture of ethyl ester of (E)-3-methyl-2-hexenoic acid and ethyl ester of (Z)-3-methyl-2-hexenoic acid.

14. The method of claim 13 wherein said mixture comprises ethyl ester of (E)-3-methyl-2-hexenoic acid and ethyl ester of (Z)-3-methyl-2-hexenoic acid in a 3:1 ratio.

15. The method of claim 14 wherein said mixture is in a liquid solution comprising 5–8 mM of the mixture of ethyl ester of (E)-3-methyl-2-hexenoic acid and ethyl ester of (Z)-3-methyl-2-hexenoic acid per milliliter of liquid.

16. The method of claim 11 wherein said at least one ester compound comprises ethyl ester of (E)-3-methyl-2-hexenoic acid.

17. The method of claim 11 wherein said at least one ester compound comprises ethyl ester of (Z)-3-methyl-2-hexenoic acid.

18. The method of claim 11 wherein said at least one ester compound comprises methyl ester of 3-methyl-2-hexenoic acid.

19. The method of claim 11 wherein said at least one ester compound comprises ethyl ester of 3-methyl-2-octenoic acid.

20. The method of claim 11 wherein said at least one ester compound comprises ethyl ester of 3-methyl-2-pentenoic acid.

21. A method of covering a body malodor wherein one of the constituents of said malodor is 3-methyl-2-hexenoic acid and wherein said method comprises the step of providing to the locality of said malodor at least one ester compound selected from the group comprising ethyl esters of 3-methyl-2-hexenoic acid, ethyl esters of 3-methyl-2-octenoic acid, ethyl esters of 3-methyl-2-pentenoic acid, and methyl esters of 3-methyl-2-hexenoic acid.

22. The method of claim 21 wherein said ethyl esters of 3-methyl-2-hexenoic acid are selected from the group comprising ethyl ester of (E)-3-methyl-2-hexenoic acid and ethyl ester of (Z)-3-methyl-2-hexenoic acid.

23. The method of claim 21 wherein said at least one ester compound comprises a mixture of ethyl ester of (E)-3-methyl-2-hexenoic acid and ethyl ester of (Z)-3-methyl-2-hexenoic acid.

24. The method of claim 23 wherein said mixture comprises ethyl ester of (E)-3-methyl-2-hexenoic acid and ethyl ester of (Z)-3-methyl-2-hexenoic acid in a 3:1 ratio.

25. The method of claim 24 wherein said mixture is in a liquid solution comprising 5–8 mM of the mixture of ethyl ester of (E)-3-methyl-2-hexenoic acid and ethyl ester of (Z)-3-methyl-2-hexenoic acid per milliliter of liquid.

26. The method of claim 21 wherein said at least one ester compound comprises ethyl ester of (E)-3-methyl-2-hexenoic acid.

27. The method of claim 21 wherein said at least one ester compound comprises ethyl ester of (Z)-3-methyl-2-hexenoic acid.

28. The method of claim 21 wherein said at least one ester compound comprises methyl ester of 3-methyl-2-hexenoic acid.

29. The method of claim 21 wherein said at least one ester compound comprises ethyl ester of 3-methyl-2-octenoic acid.

30. The method of claim 21 wherein said at least one ester compound comprises ethyl ester of 3-methyl-2-pentenoic acid.

31. A deodorant comprising at least one ester compound selected from the group comprising ethyl esters of 3-methyl-2-hexenoic acid, ethyl esters of 3-methyl-2-octenoic acid, ethyl esters of 3-methyl-2-pentenoic acid, and methyl esters of 3-methyl-2-hexenoic acid and a suitable carrier.

32. The deodorant of claim 31 wherein said ethyl esters of 3-methyl-2-hexenoic acid are selected from the group comprising ethyl ester of (E)-3-methyl-2-hexenoic acid and ethyl ester of (Z)-3-methyl-2-hexenoic acid.

33. The deodorant of claim 31 wherein said at least one ester comprises a mixture of ethyl ester of (E)-3-methyl-2-hexenoic acid and ethyl ester of (Z)-3-methyl-2-hexenoic acid.

34. The deodorant of claim 33 wherein said mixture comprises ethyl ester of (E)-3-methyl-2-hexenoic acid and ethyl ester of (Z)-3-methyl-2-hexenoic acid in a 3:1 ratio.

35. The deodorant of claim 34 wherein said mixture is in a liquid solution comprising 5–8 mM of the mixture of ethyl ester of (E)-3-methyl-2-hexenoic acid and ethyl ester of (Z)-3-methyl-2-hexenoic acid per milliliter of liquid.

36. The deodorant of claim 31 wherein said at least one ester compound comprises ethyl ester of (E)-3-methyl-2-hexenoic acid.

37. The deodorant of claim 31 wherein said at least one ester compound comprises ethyl ester of (Z)-3-methyl-2-hexenoic acid.

38. The deodorant of claim 31 wherein said at least one ester compound comprises methyl ester of 3-methyl-2-hexenoic acid.

39. The deodorant of claim 31 wherein said at least one ester compound comprises ethyl ester of 3-methyl-2-octenoic acid.

40. The deodorant of claim 31 wherein said at least one ester compound comprises ethyl ester of 3-methyl-2-pentenoic acid.

* * * * *